(12) United States Patent
Sakaguchi

(10) Patent No.: US 8,814,844 B2
(45) Date of Patent: Aug. 26, 2014

(54) ABSORBENT ARTICLE

(75) Inventor: Satoru Sakaguchi, Kanonji (JP)

(73) Assignee: Unicharm Corporation, Ehime (JP)

( * ) Notice: Subject to any disclaimer, the term of this patent is extended or adjusted under 35 U.S.C. 154(b) by 509 days.

(21) Appl. No.: 12/935,616

(22) PCT Filed: Mar. 24, 2009

(86) PCT No.: PCT/JP2009/055839
§ 371 (c)(1),
(2), (4) Date: Mar. 2, 2011

(87) PCT Pub. No.: WO2009/122970
PCT Pub. Date: Oct. 8, 2009

(65) Prior Publication Data
US 2011/0144612 A1    Jun. 16, 2011

(30) Foreign Application Priority Data

Mar. 31, 2008  (JP) ................................. 2008-094108

(51) Int. Cl.
*A61F 13/15*  (2006.01)
(52) U.S. Cl.
USPC ............ 604/391; 604/389; 604/390; 604/392
(58) Field of Classification Search
CPC ..... A61F 13/62; A61F 13/5622; A61F 13/58; A61F 13/622
USPC ............ 604/385.24, 385.29, 385.3, 389–392; 2/111, 75, 80, 109, 73, 78.1, 78.4; 24/306, 304
See application file for complete search history.

(56) References Cited

U.S. PATENT DOCUMENTS 6,110,157 A    8/2000  Schmidt
2003/0055389 A1    3/2003  Sanders et al.

FOREIGN PATENT DOCUMENTS

| EP | 2266512 A1 | 12/2010 |
|----|----|----|
| JP | 4261655 | 9/1992 |
| JP | 2000014702 | 1/2000 |
| JP | 2003180752 | 7/2003 |
| JP | 3575990 B2 | 10/2004 |
| JP | 2006305377 | 11/2006 |
| JP | 2006314771 | 11/2006 |
| JP | 2007061462 A | 3/2007 |
| WO | 0226183 A1 | 4/2002 |

OTHER PUBLICATIONS

ISR for PCT/JP2009/055839 mailed Jun. 30, 2009.
Office Action corresponding to JP 2008-094108, dated Aug. 28, 2012.

(Continued)

*Primary Examiner* — Melanie Hand
*Assistant Examiner* — Aundria Hairell
(74) *Attorney, Agent, or Firm* — Lowe Hauptman & Ham LLP

(57) ABSTRACT

Disclosed is an absorbent product wherein a pair of folded portions that can be folded back is formed on both sides in the width direction of the absorbent product on portions of a flap. On the pair of folded portions, latch members that can fasten to prescribed areas of a front waistline member or a rear waistline member are respectively disposed. The flap is connected to the front waistline member or the rear waistline member at the two ends in the width direction of the absorbent product. Between the two ends and the folded portions, non-connected regions are provided where the flap is not connected to the front waistline member or the rear waistline member.

10 Claims, 5 Drawing Sheets

(56) References Cited

OTHER PUBLICATIONS

Office Action corresponding to CN 200980100251.4, dated Aug. 31, 2012.
Extended European Search Report corresponding to EP 09727397.3, dated Nov. 16, 2012.
Office Action corresponding to EG 2010091657, dated Nov. 7, 2012.
Office Action issued Apr. 16, 2013 corresponds to Colombian patent application No. 10-134847.
Office Action issued by the Indonesian Patent Office on Dec. 21, 2012 in corresponding Indonesian Application No. W00201003771, with English translation.
Office Action issued Jun. 11, 2014, corresponds to Taiwanese patent application No. 098110755.

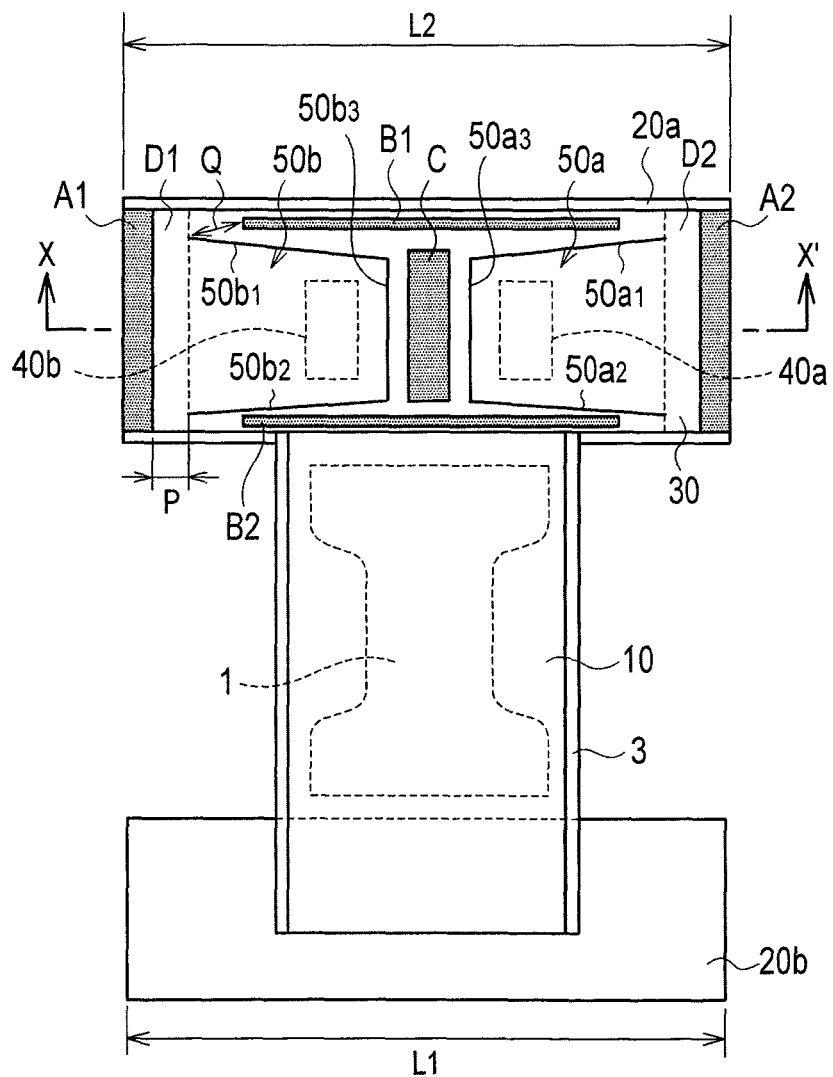
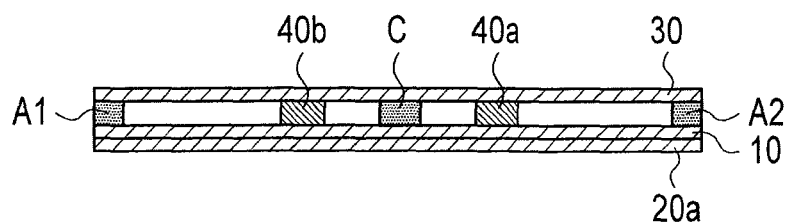

ENLARGED VIEW

ABSORBENT ARTICLE

RELATED APPLICATIONS

The present application is national phase of International Application Number PCT/JP2009/055839 filed Mar. 24, 2009, and claims priority from, Japanese Application Number 2008-094108 filed Mar. 31, 2008.

TECHNICAL FIELD

The present invention relates to an absorbent article including: a front waistline member, a rear waistline member, and a crotch member connecting the front waistline member and the rear waistline member.

BACKGROUND ART

In general, in order to be easily putted on the wearer, an open-type diaper needs to be provided with side flaps projected outwardly from an absorbent body.

As such an open-type diaper, Patent Literature 1 discloses a diaper in which sheet pieces made of members other than an absorbent body are bonded to and locked in both side edges of the absorbent body, so as to form the side flaps.

Patent Literature 1: Japanese Patent Application Publication 04-261655

DISCLOSURE OF THE INVENTION

However, in the above-described open-type diaper, the side flaps are directly bonded to the absorbent body by use of a thermal fusion bonding or an adhesive bonding such as a thermoplastic resin. Accordingly, there has been a problem that, when a flap is unfolded, or when the diaper is being putted on, tension is applied on the bonding region between the absorbent body and the side flaps (hereinafter referred to as flap(s)). Thereby the flaps are easily torn and separated from the absorbent body.

The present invention has been made in view of the aforementioned problem and an object thereof is to provide an absorbent article having a structure in which flaps are not easily torn and separated from an absorbent body.

A first aspect of the present invention is summarized as an absorbent article including a front waistline member, a rear waistline member and a crotch member that connects the front waistline member and the rear waistline member, wherein a pair of folded portions that can be respectively folded outwardly in both of a width direction of the absorbent article is formed on a part of a flap; a latch member that can be attached to and locked in a predetermined region on the front waistline member or on the rear waistline member is placed on each of the pair of folded portions and; the flap is bonded to any one of the front waistline member and the rear waistline member, in both edge portions of the absorbent article along the width direction; and a non bonding region, in which the flap is not bonded to the any one of the front waistline member and the rear waistline member, is formed between either edge portion and either folded portion located in the either edge position.

As described above, the present invention can provide an absorbent article having a structure in which flaps are not easily torn and separated from an absorbent body.

BRIEF DESCRIPTION OF DRAWINGS

FIG. 2 is a plan view of the absorbent article according to the first embodiment of the present invention.

FIG. 3 is a cross sectional view of the absorbent article taken along X-X' line, according to the first embodiment of the present invention.

PREFERRED EMBODIMENTS FOR CARRYING OUT THE INVENTION

Absorbent Article According to First Embodiment of the Present Invention

Figure 1:
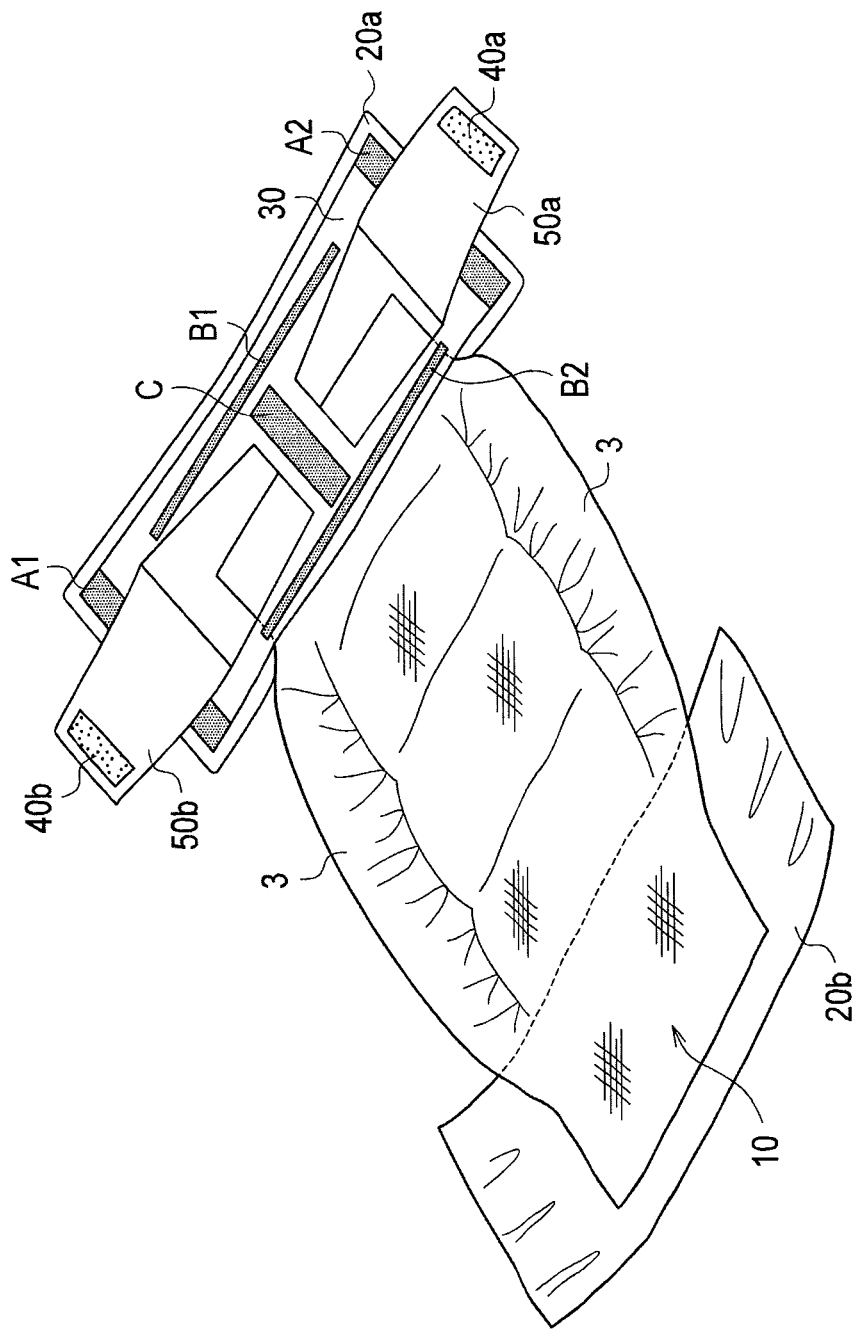
FIG. 1 is a perspective view showing an overall structure of an absorbent article according to a first embodiment of the present invention.

With reference to FIGS. 1 to 6, detailed description will be given of an absorbent article according to a first embodiment of the present invention. For example, as shown in FIG. 1, the absorbent article according to the first embodiment can be applied to an open-type diaper.

As shown in FIG. 2, the absorbent article according to the first embodiment includes: a front waistline member 20b, a rear waistline member 20a and a crotch member (absorbent body) 10 that connects the front waistline member 20b and the rear waistline member 20a.

The absorbent body 10 includes a top sheet, a back sheet and an absorber core 1. The top sheet is a liquid permeable sheet formed of a non-woven fabric. The back sheet is a liquid impermeable sheet formed of a plastic film, a laminated material consisting of a plastic film and a non-woven fabric, or the like. The absorber core 1 is interposed between the top sheet and the back sheet and bonded to at least one of the top and back sheets.

The absorber core 1 may be formed by compressing a mixture of flap pulp and particulate or fibrous super water-absorbent polymers to have a predetermined thickness or by compressing a mixture of flap pulp, particulate or fibrous super water-absorbent polymers and thermoplastic synthetic-resin fibers to have a predetermined thickness.

It is preferable that the entire surface of the absorber core 1 be covered with a tissue paper to prevent the absorber core 1 from losing its shape and the polymer particles therein from falling off. Note that the polymer particles used here may be starch particles, cellulose particles, or synthetic polymer particles.

Leak barriers 3 are respectively formed on both side edge portions of the absorbent body 10. Moreover, the front waistline member 20b and the rear waistline member 20a may have stretching/distensible properties.

Here, a length L1 of the front waistline member 20b in the width direction of the absorbent article and a length L2 of the rear waistline member in the width direction of the absorbent article are set to be equal.

As shown in FIG. 2, a flap 30 is bonded to the rear waistline member 20a. Specifically, the rear waistline member 20a and the flap 30 are bonded together along edge portions A1 and A2 in the width direction of the absorbent article, as shown in FIG. 2.

In this regard, it is preferable that the flap 30 be bonded on the rear waistline member 20 using an embossing roller or a thermo compression by ultrasonic waves, or the like. Furthermore, the thermoplastic resin may be applied along the edge portions A1 and A2 of the flap 30.

In addition, a pair of folded portions 50a and 50b is formed on a part of the flap 30. The folded portions 50a and 50b can be respectively folded outwardly in both width directions of the absorbent article.

A latch member 40a that can be attached to and locked in a predetermined region of the front waistline member 20b is placed on the folded portion 50a, while an latch member 40b that can be attached to and locked in a predetermined region of the front waistline member of 20b is placed on the folded portion 50b.

In this regard, when hook members (male members) are placed as the latch members 40a and 40b, hooked members (female members) are provided as latched members in the predetermined regions of the front waistline member 20b.

Note that, in the present embodiment, the front waistline member 20b is made of a non-woven fabric. Accordingly, the predetermined regions of the front waistline member 20b themselves can serve as the hooked members even when the hooked members are not additionally provided.

As shown in FIG. 3, the absorbent article is configured such that the latch members 40a and 40b are locked and thus the pair of folded portions 50a and 50b is temporarily bonded to the absorbent body 10 while the folded portions 50a and 50b are not folded back. Here, the absorbent article may be configured such that the pair of folded portions 50a and 50b is temporarily bonded to the absorbent body 10 by performing an embossing or the like instead of using the latch members 40a and 40b while the folded portions 50a and 50b are not folded back.

In addition, the pair of folded portions 50a and 50b includes: at least any one of a first cut portion (first slit) and a first cut-out portion (first trimming), and at least any one of a second cut portion (second slit) and a second cut-out portion (second trimming). Here, the first cut portion and the first cut-out portion are formed to extend in the longitudinal direction of the absorbent article while the second cut portion and second cut-out portion are formed to extend in the width direction of the absorbent article.

For example, in an example shown in FIG. 2, the folded portion 50a is formed of a first cut portion 50a3 and two second cut portions 50a1 and 50a2. The first cut portion 50a3 is formed along the longitudinal direction of the absorbent article while each of the second cut portions 50a1 and 50a2 is formed along the width direction of the absorbent article.

Meanwhile, the folded portion 50b is formed of a first cut portion 50b3 and two second cut portions 50b1 and 50b2. The first cut portion 50b3 is formed along the longitudinal direction of the absorbent article while each of the second cut portions 50b1 and 50b2 is formed along the width direction of the absorbent article.

Note that each of the first cut portions 50a3 and 50b3 and the second cut portions 50a1, 50a2, 50b1 and 50b2 may be configured of a cuttable piece such as a perforated line.

Moreover, each of the first cut portions 50a3 and 50b3 and the second cut portions 50a1, 50a2, 50b1 and 50b2 may be a straight line or a curved line.

The flap 30 is bonded to the rear waistline member 20a in both edge portions A1 and A2 in the width direction of the absorbent article.

Moreover, the flap 30 may be bonded to the rear waistline member 20a in the edge portions B1 and B2 of the absorbent article along the longitudinal direction.

In addition, the flap 30 may be bonded to the rear waistline member 20a in a region C formed between the pair of folded portions 50a and 50b.

Note that, non bonding regions D1 and D2, in which the flap 30 is not bonded to the rear waistline member 20a, are formed in a space between the folded portion 50b and the edge portion A1 of the absorbent article along the width direction, and a space between the folded portion 50a and the edge portion A2 of the absorbent article along the width direction, respectively. In other words, the non bonding region is formed between either edge portion (A1 for example) and either folded portion (50b for example) located in the edge position (A1).

Figure 4:
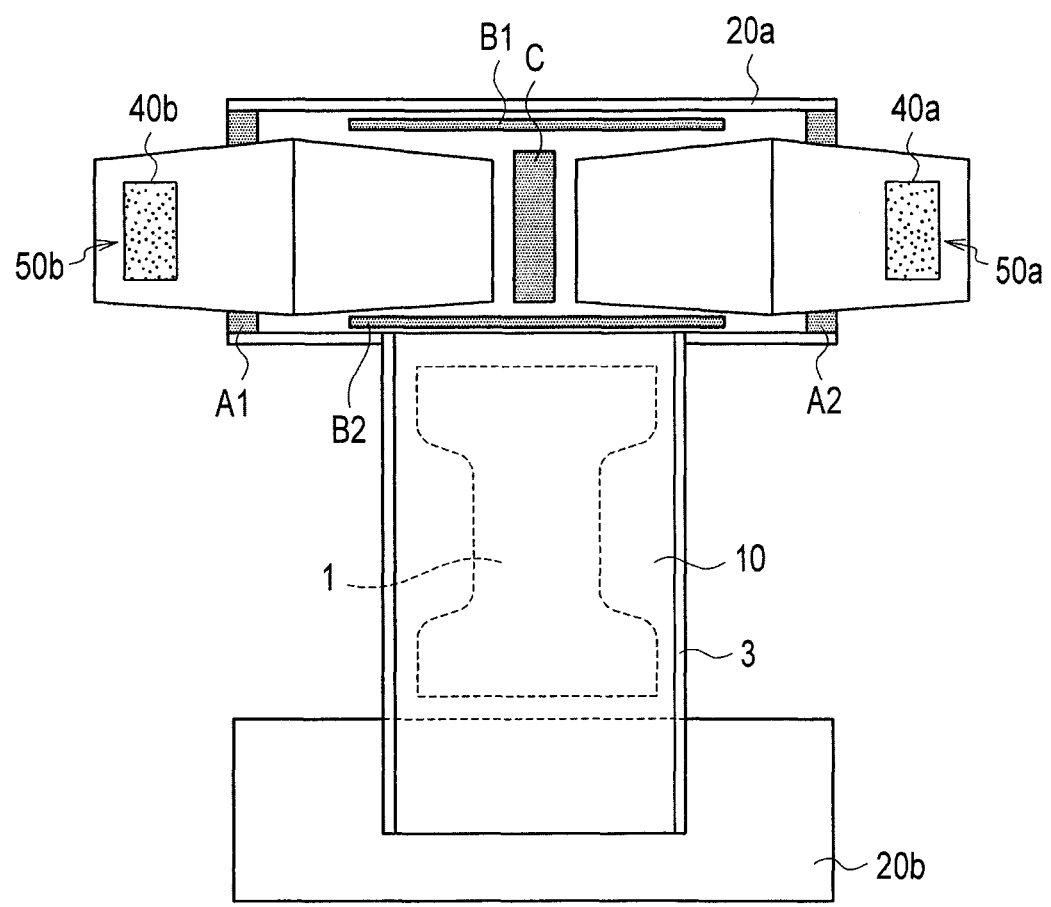
FIG. 4 is a plan view of an unfolded state of the absorbent article according to the first embodiment of the present invention.

Here, consider the case where the pair of folded portions 50a and 50b is respectively folded back outwardly in both width directions of the absorbent article, like hinges as shown in FIG. 4. Even in this case, the flap 30 is not entirely folded back by cutting the absorbent article until the longitudinal direction end.

Moreover, when the pair of folded portions 50a and 50b is respectively folded back outwardly in both width directions of the absorbent article, like hinges, tension applied to the bonding regions A1 and A2 each formed between the flap 30 and the rear waistline member 20a is absorbed by the non bonding regions D1 and D2 each having a length P in the width direction of the absorbent article.

In particular, the non bonding regions D1 and D2 can provide a cushion function to absorb a momentary tension caused when the pair of folded portions 50a and 50b is respectively folded back in both of width directions of the absorbent article, like hinges. Moreover, when the pair of folded portions 50a and 50b is respectively folded back outwardly in both of width directions of the absorbent article, like hinges, a slack (gap) of materials is generated between the rear waistline member 20a and each region Q. The region Q is formed between each edge portions of the bonding regions B1, B2 and each edge portions 100a, 100b of the second cut portions (or second cut-out portions) 50a1, 50a2, 50b1 and 50b2 on the non bonding regions D1 and D2 side (see FIG. 5). This slack of materials can absorb tension applied to the bonding regions A1 and A2 formed between the flap 30 and the rear waistline member 20a.

Further, the edge portions 100a and 100b of the second cut portions (or second cut-out portions) 50a1, 50a2, 50b1 and 50b2 on the non bonding regions D1 and D2 side, may be treated to be curved.

Figure 5:
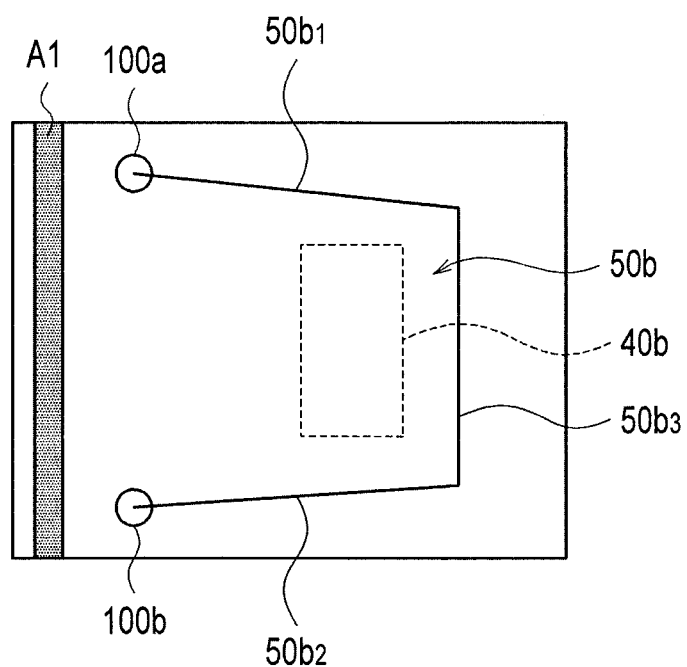
FIG. 5 is a diagram for illustrating a folded portion formed on a flap in the absorbent article according to the first embodiment of the present invention.

For example, as shown in FIG. 5, the edge portions 100a and 100b of the second cut portions (or second cut-out portions) 50a1, 50a2, 50b1 and 50b2 on the non bonding regions D1 and D2 side, may be treated to have a circular shape.

Figure 6:
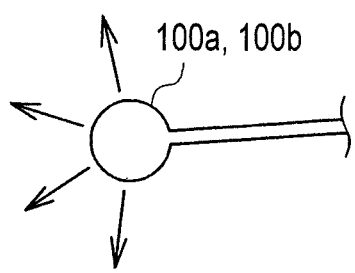
FIG. 6 is an enlarged view of an edge portion of a cut portion constituting the folded portion formed on the flap in the absorbent article according to the first embodiment of the present invention.

In this case, as shown in FIG. 6, tension applied to each of the bonding regions A1 and A2, which are formed between the flap 30 and the rear waistline member 20a, is distributed outwardly from each of the center of the circles.

Note that, in the foregoing example, the flap 30, on which the latch members 40a and 40b that can be attached to and locked in the predetermined regions of the front waistline member 20b are placed, is placed on the rear waistline member 20a. However, the present invention is not limited to this example. The flap 30, on which the latch members 40a and 40b that can be attached to and locked in the predetermined regions of the rear waistline member 20a are placed, may be placed on the front waistline member 20b.

Further, the flap 30 may be bonded to the any one of the front waistline member 20b and the rear waistline member 20a to cover edge portions of the absorbent body 10 (crotch member).

In the absorbent article according to the first embodiment of the present invention, the pair of folded portions 50a and 50b is formed so that the flap 30 is not entirely folded back by cutting the absorbent article until the longitudinal direction end. Accordingly, the user may easily unfold the manufactured diaper. Further, it is possible to prevent a situation that the continuum of the flaps 30 is cut on the manufactured line and cannot be continuously transported, and a situation that the high level controls are required and thereby the manufacturing facility becomes complicated.

Moreover, the absorbent article according to the first embodiment of the present invention, the absorbent article includes the non bonding regions D1 and D2 each having the length P in the width direction of the absorber. Further, the absorbent article includes the region Q formed between the edge portions of the bonding region B1, B2 and the edge portions 100a, 100b of the second cut portions (or second cut-out portions) 50a1, 50a2, 50b1, 50b2 on the non bonding regions D1 and D2 side. Accordingly, tension applied to the bonding regions A1 and A2 between the flap 30 and the rear waistline member 20a can be absorbed when the pair of folded portions 50a and 50b is respectively folded back outwardly in both of width directions of the absorbent article. Therefore, the possible occurrence in which the folded portions 50a and 50b functioning as flaps is unexpectedly torn to be separated from the rear waistline member 20a can be reduced.

Modified Example 1

Figure 7:
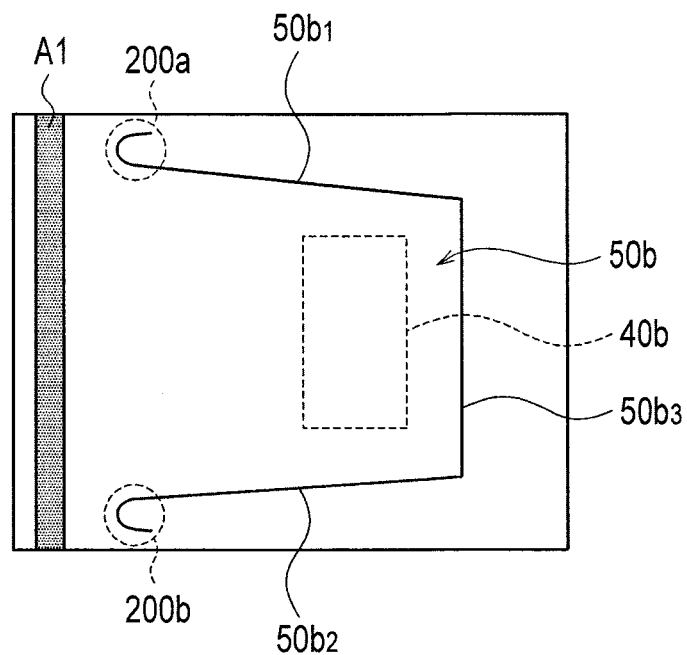
FIG. 7 is a diagram for illustrating a folded portion formed on a flap in the absorbent article according to a modified example 1 of the present invention.

With reference to FIG. 7, description will be given of an absorbent article according to a modified example 1 of the present invention. Hereinafter, the absorbent article according to the modified example 1 of the present invention will be described mainly focusing on the differences from the absorbent article according to the first embodiment of the present invention.

For example, in the absorbent article according to the modified example 1 of the present invention, edge portions 200a and 200b of the second cut portions 50a1, 50a2, 50b1 and 50b2 on the non bonding regions D1 and D2 side may be smoothly curved toward the outside of the folded portions 50a and 50b, respectively, as shown in FIG. 7.

In this case as well, tension applied to the bonding regions A1 and A2, which are formed between the flap 30 and the rear waistline member 20a, is distributed outwardly from each of the center of the shape of the edge portions 200a and 200b.

Modified Example 2

Figure 8:
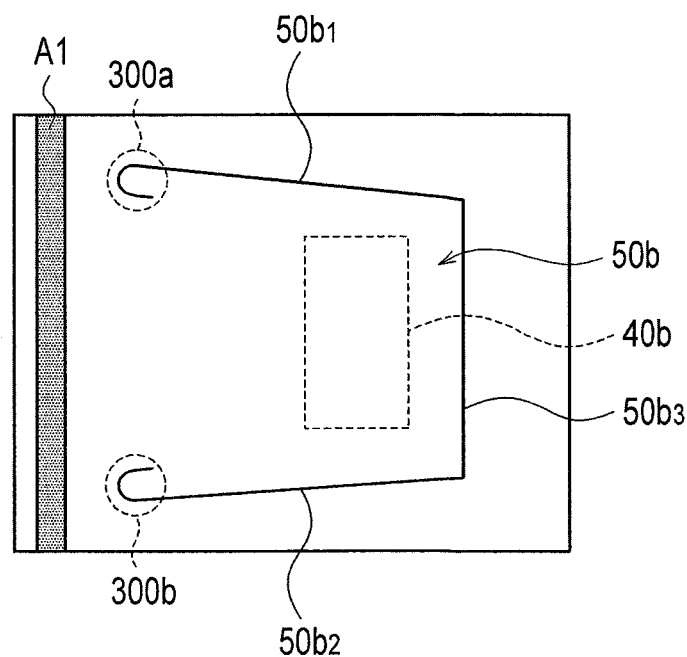
FIG. 8 is a diagram for illustrating a folded portion formed on a flap in the absorbent article according to a modified example 2 of the present invention.

With reference to FIG. 8, description will be given of an absorbent article according to a modified example 2 of the present invention. Hereinafter, the absorbent article according to the modified example 2 of the present invention will be described mainly focusing on the differences from the absorbent article according to the first embodiment of the present invention.

For example, in the absorbent article according to the modified example 2 of the present invention, edge portions 300a and 300b of the second cut portions 50a1, 50a2, 50b1 and 50b2 on the non bonding regions D1 and D2 side may be smoothly curved toward the inside of the folded portions 50a and 50b, respectively, as shown in FIG. 8.

In this case as well, tension applied to the bonding regions A1 and A2, which are formed between the flap 30 and the rear waistline member 20a, is distributed outwardly from each of the center of the shape of the edge portions 300a and 300b.

As described above, the present invention has been described in detail by using the above-described embodiments. However, it is obvious for a person skilled in the art that the present invention is not limited to the embodiments described in this specification. The present invention can be implemented as a modification and an amended embodiment without departing from the content and scope of the present invention which is defined by the description of the scope of claims. Accordingly, the description of the present invention is intended to give description as an example and does not have any meaning to limit the present invention.

Note that the entire contents of the Japanese Patent Applications No. 2008-094108, filed on Mar. 31, 2008 are incorporated herein by reference.

INDUSTRIAL APPLICABILITY

As has been described in the above, the present invention is useful for the absorbent article, because there can be provided the absorbent article having a structure in which flaps are not easily separated from an absorbent body.

The invention claimed is:

1. An absorbent article including a front waistline member, a rear waistline member and a crotch member connecting the front waistline member and the rear waistline member, wherein
a pair of folded portions that can be folded outwardly in both of a width direction of the absorbent article is formed on a part of a flap;
a latch member that can be attached to and locked in a predetermined region on the front waistline member or on the rear waistline member is placed on each of the pair of folded portions;
the flap is bonded to any one of the front waistline member and the rear waistline member, in both first edge portions of the absorbent article along the width direction; and
a non bonding region, in which the flap is not bonded to the any one of the front waistline member and the rear waistline member, is formed between either first edge portion and either folded portion located in the either edge position,
the flap is bonded to one of the front waistline member and the rear waistline member, in both second edge portions of the absorbent article along a longitudinal direction of the absorbent article,
each of the pair of folded portions includes
either a first cut portion or a first cut-out portion, and
a pair of either a second cut portion or a second cut-out portion,
the pair of the second cut portion and the second cut-out portion both extend along the width direction of the absorbent article, and
the first cut portion and the first cut-out portion both extend along the longitudinal direction of the absorbent article, and
an end of each of the second cut-out portion or the second cut portion extends back toward the first cut portion or the first cut-out portion.

2. The absorbent article according to claim 1, wherein the flap is bonded to one of the front waistline member and the rear waistline member, in a region between the pair of folded portions.

3. The absorbent article according to claim 1, wherein the flap is bonded to one of the front waistline member and the rear waistline member to cover edge portions of the crotch member.

4. The absorbent article according to claim 1, wherein a dimension of the front waistline member in the width direction of the absorbent article is equal to a dimension of the rear waistline member in the width direction of the absorbent article.

5. The absorbent article according to claim 1, wherein each of the folded portions is configured to be folded outwardly along a side edge of the corresponding non bonding region.

6. The absorbent article according to claim 1, wherein a dimension of the non bonding region in a longitudinal direction of the absorbent article is larger than a dimension of the folded portions in the longitudinal direction.

7. The absorbent article according to claim 1, wherein the folded portions comprises perforated lines opposed to each other and extending in the longitudinal direction.

8. The absorbent article according to claim 1, wherein the crotch member includes an absorbent core, and the flap does not overlap the absorbent core.

9. The absorbent article according to claim 1, wherein a dimension of the front waistline member between two front waistline side edges opposite to each other in the width direction is equal to a dimension of the rear waistline member between two rear waistline side edges opposite to each other in the width direction.

10. The absorbent article according to claim 1, wherein
the first edge portions of the flap include edges opposing each other in the width direction, and
the edges of the first edge portions of the flap are flush with edges of one of the front waistline member or the rear waistline member to which the flap is fixed.

\* \* \* \* \*